United States Patent [19]
Edwards et al.

[11] Patent Number: 5,370,624
[45] Date of Patent: Dec. 6, 1994

[54] CATHETER WITH DEACTIVATABLE SIDE PORT

[75] Inventors: Floyd V. Edwards, Sandy; Gerald H. Peterson, Salt Lake City, both of Utah

[73] Assignee: Becton Dickinson and Company, Franklin Lakes, N.J.

[21] Appl. No.: 121,006

[22] Filed: Sep. 14, 1993

[51] Int. Cl.$^5$ .............................................. A61M 5/178
[52] U.S. Cl. ........................... 604/169; 604/110; 604/247; 604/248; 604/284; 137/384.2; 137/385; 137/605
[58] Field of Search .................. 604/236, 248, 30, 32, 604/44, 45, 51, 52, 82, 83, 89, 110, 164, 167, 169, 236, 247, 248, 283, 284; 137/605, 384.2, 383, 385

[56] References Cited
U.S. PATENT DOCUMENTS

| | | | |
|---|---|---|---|
| 2,261,213 | 11/1941 | Biermann | 604/236 |
| 2,854,027 | 9/1958 | Kaiser et al. | 604/83 |
| 3,081,770 | 3/1963 | Hunter | 604/44 |
| 3,416,567 | 12/1968 | von Dardel et al. | 604/83 |
| 3,774,604 | 11/1973 | Danielsson | 604/169 |
| 3,856,020 | 12/1974 | Kovac | 604/169 |
| 4,311,136 | 12/1982 | Weikl et al. | 604/284 |
| 4,954,130 | 9/1990 | Edwards | 604/169 |
| 5,098,405 | 3/1992 | Peterson et al. | 604/256 |
| 5,098,410 | 3/1992 | Kerby et al. | 604/256 |
| 5,211,633 | 5/1993 | Stouder, Jr. | 604/167 |

*Primary Examiner*—C. Fred Rosenbaum
*Assistant Examiner*—Mark Bockelman
*Attorney, Agent, or Firm*—Michael G. Schwarz; Eric M. Lee

[57] ABSTRACT

A catheter having a side port for selective infusion of fluids is disclosed. The side port may be deactivated so that the catheter can be used as a non-side port catheter. The side port is rotable about the catheter housing to; block off access to the catheter lumen from the side port when the side port is deactivated. The catheter is also provided with a valve to facilitate the selective infusion of fluid from the side port into the catheter lumen.

10 Claims, 5 Drawing Sheets

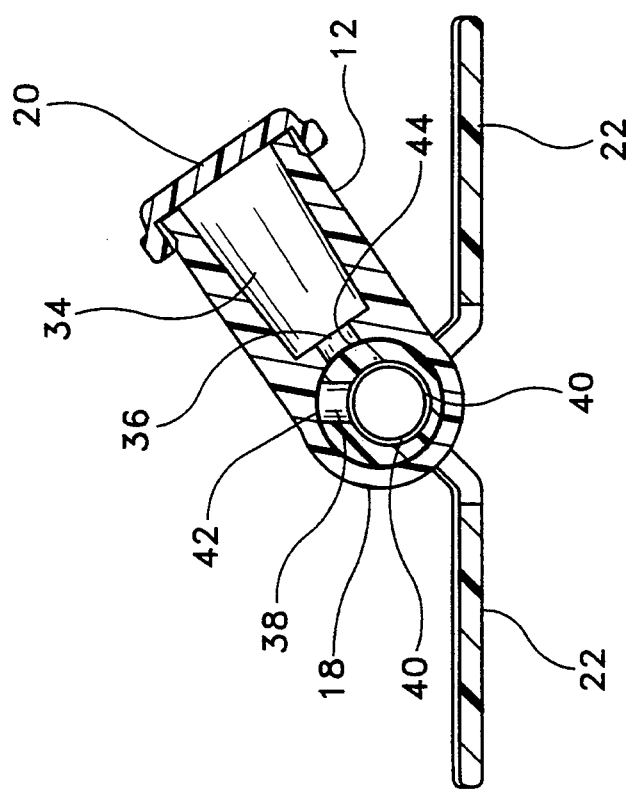
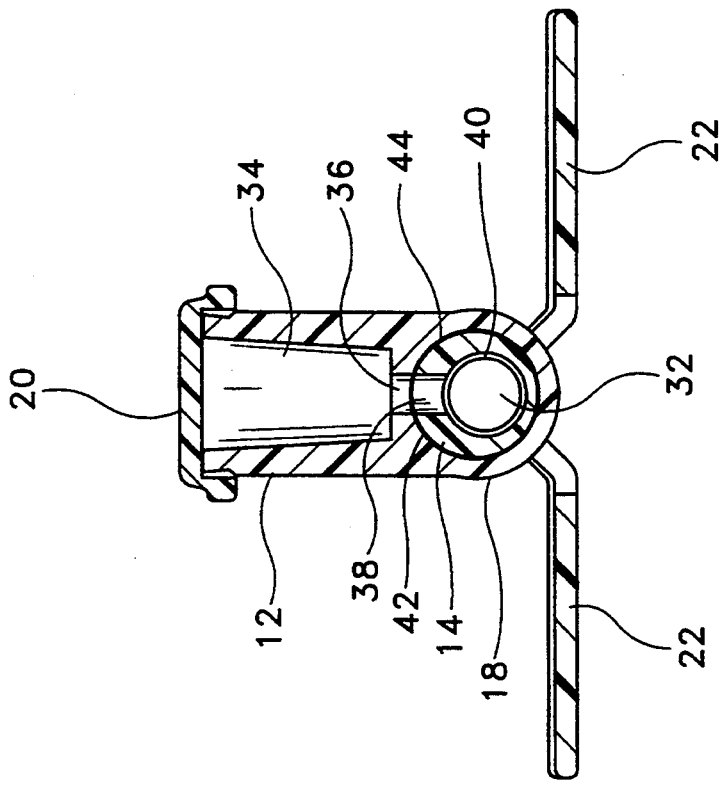
FIG-3
FIG-4

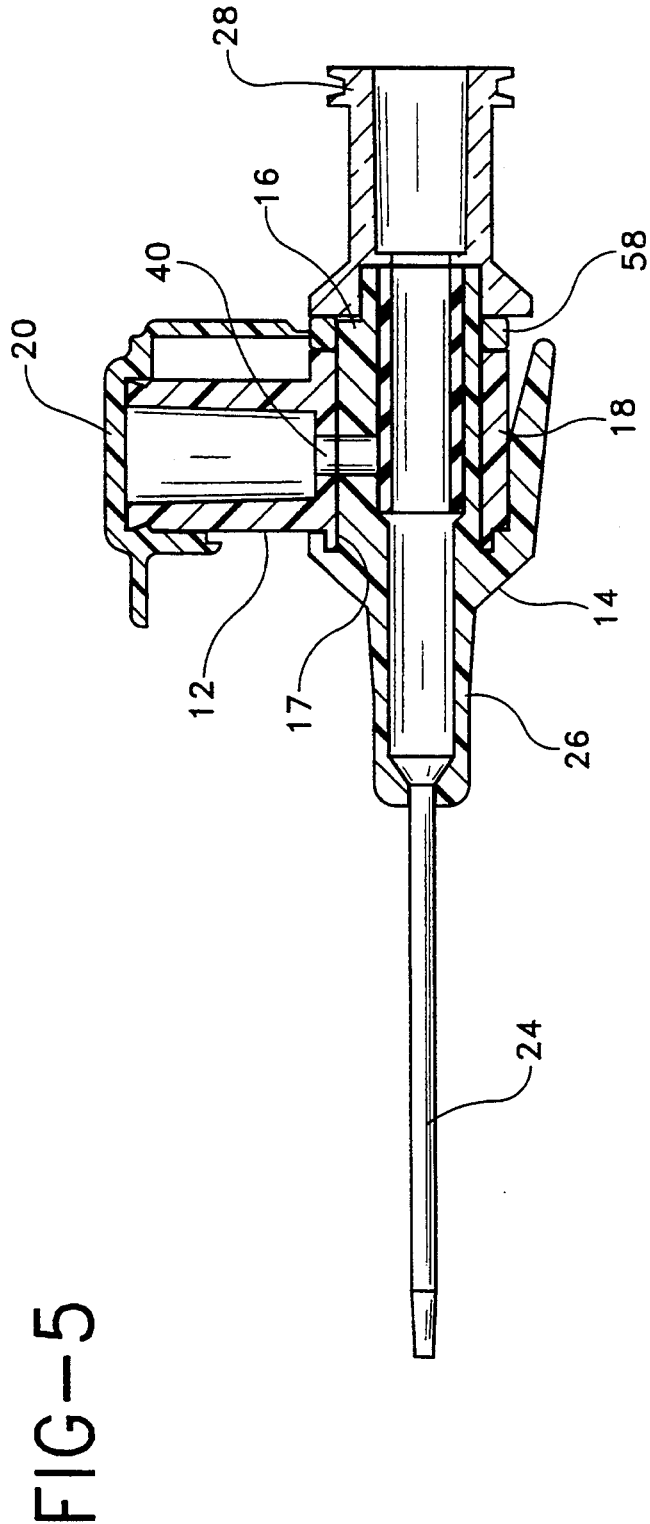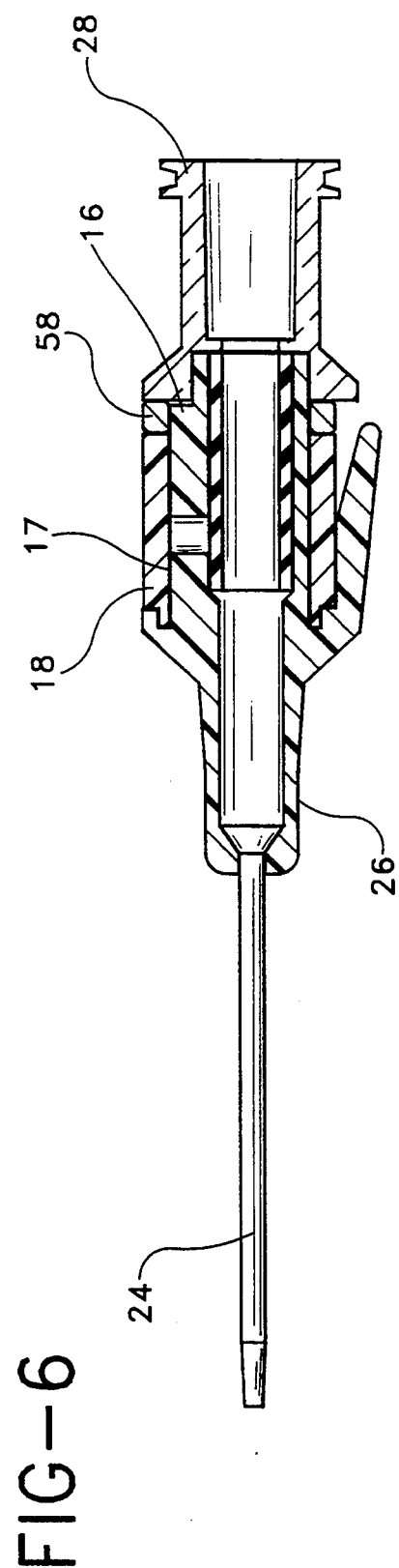

CATHETER WITH DEACTIVATABLE SIDE PORT

BACKGROUND

1. Field of the Invention

This invention relates to catheters in general, and in particular to catheters having adapters to facilitate the selective infusion of medication by means of a side port.

2. Background

Catheters having adapters to facilitate selective infusion of medications and the like into a patient's body are known in the art. An example of such a device is the Adsyte ® catheter, produced by Becton, Dickinson and Company of Franklin Lakes, New Jersey. A full description of a catheter adapter having a side port may be found in U.S. Pat. No. 5,098,405 which is incorporated herein by reference.

The Adsyte ® catheter and that described in U.S. Pat. No. 5,098,405 include a housing having a side port. The side port is designed to facilitate the insertion of a syringe for the selective infusion of fluid. When the syringe is inserted into the side port and the plunger is depressed, a valve in the catheter housing is opened and fluid may be infused. When the pressure on the plunger is relaxed, the valve closes. If the catheter is to remain in the vessel for extended periods, there is a risk of microbial development since access to the vessel is restricted only by the valve and a protective cap which may be placed on the side port.

It is an object of this invention to provide a catheter with a side port to allow selective infusion of medications and the like. The side port is able to be deactivated, thereby preventing its further use.

It is a further object of this invention to provide a catheter which can function as a side port catheter as well as a normal, non-side port catheter.

SUMMARY OF THE INVENTION

The invention is embodied in a medical catheter assembly which has a housing having a passage extending through it. The passage has an axial lumen having first and second ends and through which fluid can flow and is provided with an opening disposed between the first end and the second end. A side port for providing access to the passage is attached to the housing. The side port is provided with a cavity for gaining access to the passage via the opening such that fluid can be infused into the passage from the side port. The side port may be selectively deactivated such that when the side port is deactivated, fluid flow between the side port and the passage is inhibited.

In a specific embodiment of the invention, the side port is rotatable on the housing from an activated position in which fluid may be infused through the side port into the passage to a deactivated position in which fluid cannot be infused through the side port into the housing. In a further embodiment, a seal between the side port and the housing is provided to act as a barrier to prevent the entry of contaminants into the passage when the side port is in the deactivated position. In another embodiment, a latch is provided to lock the side port in the deactivated position.

BRIEF DESCRIPTION OF THE DRAWINGS

FIG. 3 is a cross-sectional view through section 3—3 of FIG. 1;

FIG. 4 is a cross-sectional view through section 3—3 of FIG. 2;

FIG. 5 is a cross-sectional view through section 5—5 of FIG. 1;

FIG. 6 is a cross-sectional view through section 6—6 of FIG. 2; and

DETAILED DESCRIPTION OF THE DRAWINGS

Figure 1:
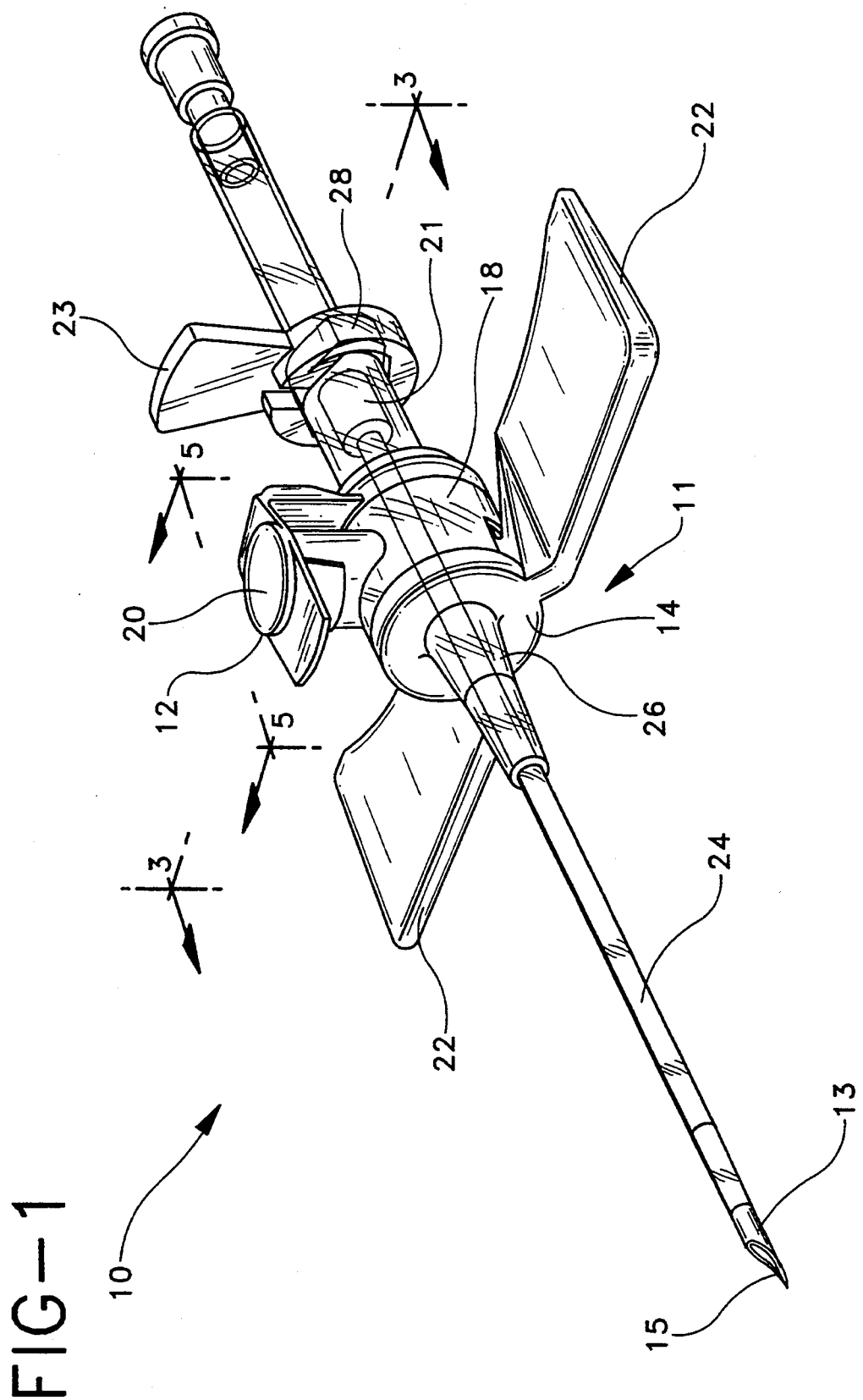
FIG. 1 is a perspective view of a preferred embodiment of the invention.
Figure 2:
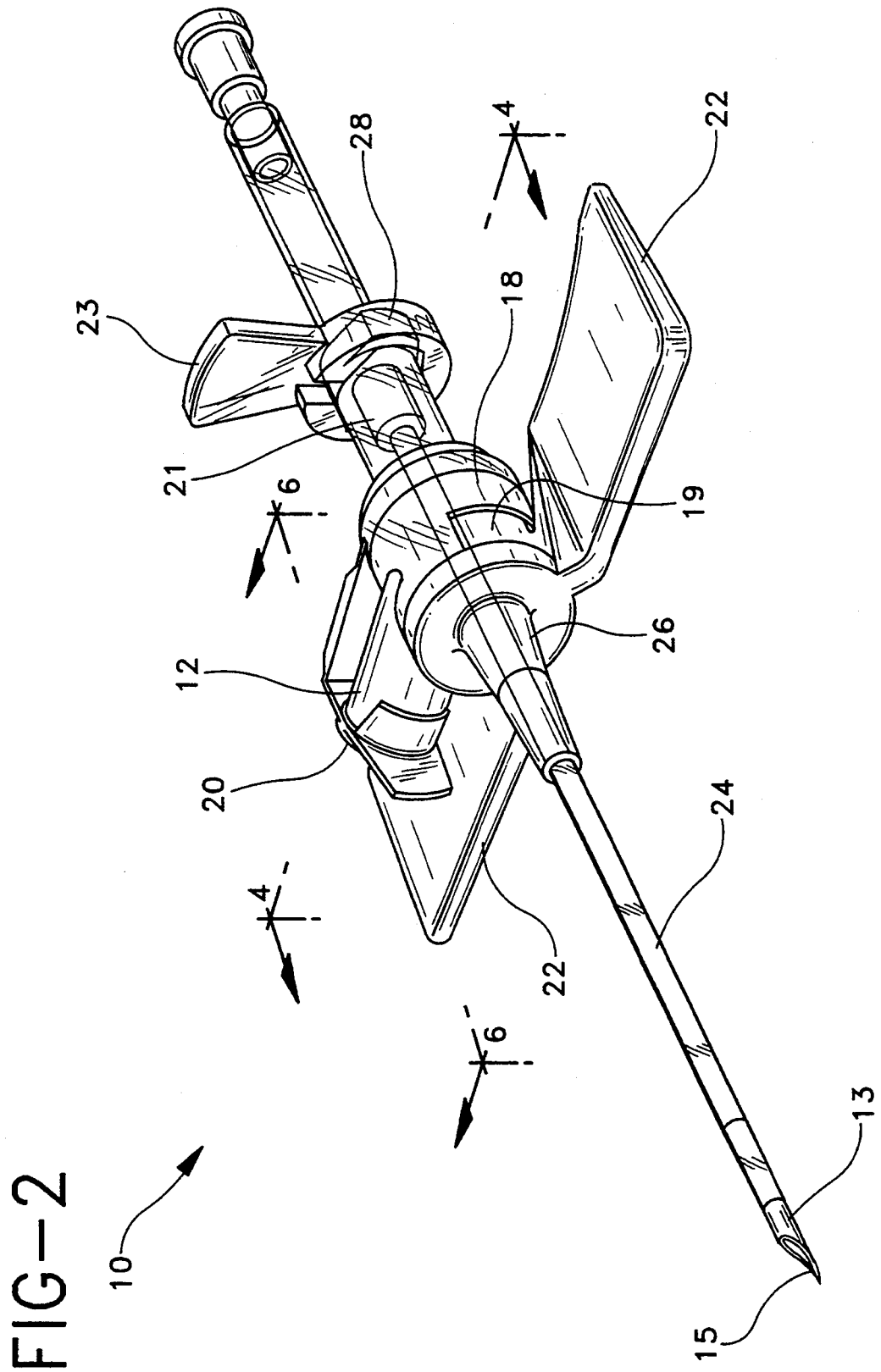
FIG. 2 is a perspective view of the preferred embodiment of the invention with the side port in its deactivated state.
Figure 7:
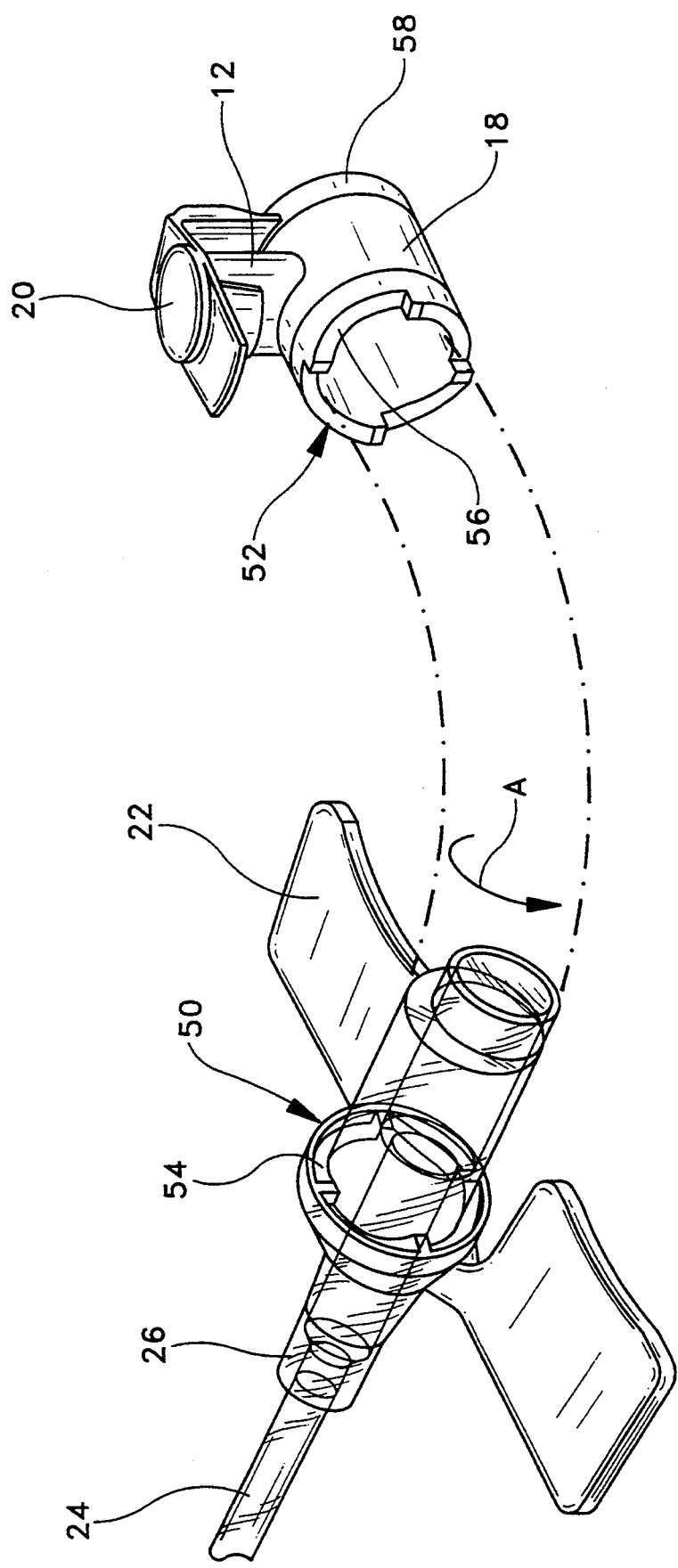
FIG. 7 is an exploded view of the invention showing the side port locking mechanism.

Catheter introducer 10 is shown in perspective view in FIGS. 1 and 2. FIG. 1 shows the catheter introducer with side port 12 in its activated state. Catheter introducer 10 has a catheter assembly 11 made up of housing 14 and cannula 24. Slidably mounted coaxially in housing 14 and cannula 24 is introducer needle 13 having distal sharp tip 15 and proximal hub 21. Hub 21 is provided with thumb tab 23 to facilitate insertion of needle 13. Tube 24 is secured to distal end 26 of housing 14. Luer connector 28 is secured to distal end 26 of housing 14. Side port 12 is shown in its deactivated state in FIG. 2.

Housing 14 is formed by a generally cylindrical robe 16 having recessed track 17 (see also FIG. 5). Surrounding tube 16 is rotatable sheath 18 which carries side port 12. Sheath 18 rides in track 17. Sheath 18 is provided with cutaway 19 to facilitate its rotation about housing 14 (see FIG. 2). Side port 12 is provided with cap 20 which may be used to cover and uncover side port 12. Attached to housing 14 are wings 22 which are provided to facilitate the fastening of invention 10 to the skin of a patient. Wings 22 also interact with side port 12 to allow unidirectional rotation of sheath 18 through a limited arc. When side port 12 is deactivated, side port abuts wing 22.

Passage 32 extends through housing 14 (see FIGS. 3, 4, 5 and 6). Valve 40 is positioned within passage 32 (see FIG. 5). Sheath 18 surrounds housing 14. Within side port 12 is cavity 34 into which a syringe nozzle may be inserted. Adjoining cavity 34 is narrow cavity 36 in sheath 18 which is co-linear with opening 38 of housing 14 when side port 12 is in its activated state. When side port 12 is in the activated position shown in FIGS. 3 and 5, cavity 34 is in fluid communication with passage 32 via cavity 36 and opening 38.

When a syringe nozzle is inserted into cavity 34, the pressure of fluid from the syringe will open valve 40 (FIG. 5), thereby permitting fluid to flow into passage 32. Removal of the fluid pressure will close valve 40.

To move side port 12 into its deactivated position as shown in FIGS. 2, 4 and 6 side port 12 (and thus sheath 18) is rotated about housing 14 on track 17 so that cavity 36 is no longer co-linear with opening 38 as shown in FIGS. 4 and 6. Instead, wall 42 of sheath 18 covers opening 38, and wall 44 of housing blocks off cavity 36. Thus fluid cannot flow from opening 34 into passage 32. A seal is created by the interaction of sheath 18 with wall 44 of housing 18 when sheath 18 is sufficiently rotated.

To ensure that side port 12 cannot be reactivated after it has been deactivated, a locking mechanism is provided. Housing 14 is provided with ratchet 50. Sheath 18 is provided with matching ratchet 52. Ratchets 50 and 52 are provided respectively with ramped teeth 54 and 56 which are oriented such that rotation of sheath 18 into the deactivated position, side port 12 wing 22, preventing further rotation of sheath 18 only in the direction of arrow A. Side port 12 is thus maintained in the deactivated state. Ratchets 50 and 52 are kept in contact by means of resilient member 58 to which cap 20 is secured. Resilient member 58 is generally in the form of an annular washer surrounding housing 14. It is held in place by the pressure of luer connector 28 forming proximal end 30 of housing 14. The above described mechanism allows side port 12 to be in a first detent position (activated) shown in FIG. 1 and to move into a second detent position (deactivated) shown in FIG. 2. Once in the second position, side port 12 cannot readily be moved back into its activated state.

When side port 12 is in its inactive state, invention 10 may be used as a conventional non-side port catheter without the risk of contamination of passage 32 through opening 38, since opening 38 is closed. Thus, the invention provides a catheter with a deactivatable side port which could also be used as a non-side port catheter.

The embodiment above is intended to be exemplary and not limiting. The full scope of the invention is delineated by the claims.

What is claimed is:

1. A medical catheter introducer assembly comprising:
    a needle;
    a catheter assembly comprising a cannula disposed about the needle and a housing to the cannula, the housing having proximal and distal ends;
    a passage extending through the housing from the proximal end to the distal end;
    a side port secured to the housing and rotatable between an inactive position and an active position for providing access to the passage, via an opening in the housing such that fluid can be infused through the side port and into the passage;
    means for selectively moving the side port from the active position into the inactive position such that when the side port is in the inactive position, fluid flow between the side port and the passage is inhibited; and
    a ratchet positioned between the sideport and the housing for locking the side port in the inactive position.

2. The assembly of claim 1 wherein the means for selectively moving the side port closes the opening when the side port is in the inactive position.

3. The assembly of claim 1 wherein the means for selectively moving the side port comprises a rotatable sheath fitting at least partially around the housing.

4. The assembly of claim 1 further comprising a valve disposed between the side port and the passage to selectively inhibit fluid communication through the opening and into the passage.

5. A catheter introducer assembly comprising:
    a catheter assembly comprising a housing having proximal and distal ends and a cannula attached to the proximal end, the housing having a passage extending between the proximal and distal ends in fluid communication with the cannula;
    a side port rotatably mounted on the housing, the side port being moveable between a first position in which the side port provides access to the passage via an opening and a second position in which access to the passage via the side port is blocked; and
    a ratchet connected to the side port for engaging the housing to prevent the side port from being moved from the second position into the first position.

6. The catheter introducer assembly of claim 5 further comprising a sheath mounted rotatably on the housing, the side port being mounted on the sheath such that the side port is rotated between the first and second positions.

7. The catheter introducer of claim 5 further comprising means for locking the side port in the second position once it has moved from the first position into the second position.

8. A method of using a catheter having a housing and a cannula attached thereto, the housing having a passage extending therethrough and in fluid communication with the cannula, a side port rotatably mounted on the housing, the side port being moveable between a first position in which the side port provides access to the passage via the opening and a second position in which access to the passage via the side port is blocked and a ratchet for locking the side port in the second position, the method comprising the steps of:
    introducing the catheter into a vessel;
    moving the side port from the first position in which fluid can be infused through the side port to the second position in which fluid cannot be infused.

9. The method of claim 8 further comprising the step of locking the side port in the inactive position.

10. A catheter introducer assembly comprising:
    a catheter assembly having a housing with proximal and distal ends and a cannula attached to the proximal end, the housing having a passage extending between the proximal and distal ends in fluid communication with the cannula;
    a side port mounted on a sheath that is rotatably mounted on the housing, the sheath being rotatable between a first position in which the side port provides access to the passage via an opening and a second position in which access to the passage via the side port is blocked; and
    a ratchet between the sheath and the housing for permitting the sheath to be rotated into the second position from the first position but not vice versa.

* * * * *